(12) United States Patent
Chow et al.

(10) Patent No.: US 6,413,401 B1
(45) Date of Patent: Jul. 2, 2002

(54) VARIABLE CONTROL OF ELECTROOSMOTIC AND/OR ELECTROPHORETIC FORCES WITHIN A FLUID-CONTAINING STRUCTURE VIA ELECTRICAL FORCES

(75) Inventors: Calvin Y. H. Chow, Portola Valley; J. Wallace Parce, Palo Alto, both of CA (US)

(73) Assignee: Caliper Technologies Corp., Mountain View, CA (US)

(*) Notice: Subject to any disclaimer, the term of this patent is extended or adjusted under 35 U.S.C. 154(b) by 0 days.

(21) Appl. No.: 09/214,127

(22) PCT Filed: Jul. 3, 1997

(86) PCT No.: PCT/US97/12930

§ 371 (c)(1),
(2), (4) Date: Jul. 29, 1999

(87) PCT Pub. No.: WO98/00707

PCT Pub. Date: Jan. 8, 1998

Related U.S. Application Data

(63) Continuation-in-part of application No. 08/678,436, filed on Jul. 3, 1996, now Pat. No. 5,800,690.

(51) Int. Cl.[7] .......................... G01N 27/26; G03C 5/00; H01B 13/00; H01S 4/00

(52) U.S. Cl. ....................... 204/602; 204/603; 430/314; 216/18; 29/592.1

(58) Field of Search ................................. 204/450, 451, 204/452, 456, 466, 600, 601, 606, 616; 430/314; 216/16–18; 29/825, 592.1, 603.16, 603.1, 603.19, 603.7, 603.13

(56) References Cited

U.S. PATENT DOCUMENTS

| | | | |
|---|---|---|---|
| 3,712,859 A | 1/1973 | Dilworth, III | 204/299 |
| 3,906,333 A | 9/1975 | Kalmanash | 323/17 |

(List continued on next page.)

FOREIGN PATENT DOCUMENTS

| | | | |
|---|---|---|---|
| DE | 24 12 956 | 10/1975 | |
| DE | 27 08 255 | 8/1978 | |
| EP | 0 035 878 | 9/1981 | G01N/27/26 |
| EP | 0 070 963 | 2/1983 | G01N/27/26 |
| EP | 0 365 321 | 4/1990 | G01N/27/26 |
| EP | 0 544 969 | 6/1993 | G01N/27/447 |
| EP | 0 629 853 | 12/1994 | G01N/27/447 |
| WO | WO 94/05414 | 3/1994 | B01F/11/02 |
| WO | WO 95/10040 | 4/1995 | G01N/27/447 |
| WO | WO 96/04547 | 2/1996 | G01N/27/00 |
| WO | WO 97/02357 | 1/1997 | C12P/19/34 |

OTHER PUBLICATIONS

Jacobson et al., "Effects of Injection Schemes and Column Geometry on the Performance of Microchip Electrophoresis Devices," *Anal. Chem.* (1994) 66:1107–1113 Apr. 2.

(List continued on next page.)

Primary Examiner—T. Tung
Assistant Examiner—Alex Noguerola
(74) Attorney, Agent, or Firm—Matthew B. Murphy; Andrew L. Filler

(57) ABSTRACT

In a microfluidic system using electrokinetic forces, the present invention uses electrical current or electrical parameters, other than voltage, to control the movement of fluids through the channels of the system. Time-multiplexed power supplies also provide further control over fluid movement by varying the voltage on an electrode connected to a fluid reservoir of the microfluidic system, by varying the duty cycle during which the voltage is applied to the electrode, or by a combination of both. A time-multiplexed power supply can also be connected to more than one electrode for a savings in cost.

15 Claims, 6 Drawing Sheets

U.S. PATENT DOCUMENTS

| | | | | |
|---|---|---|---|---|
| 4,816,123 | A | * 3/1989 | Ogan et al. | 264/272.13 |
| 4,908,112 | A | 3/1990 | Pace | 204/299 R |
| 5,126,022 | A | 6/1992 | Soane et al. | 204/180.1 |
| 5,194,133 | A | 3/1993 | Clark et al. | 204/299 R |
| 5,286,356 | A | 2/1994 | Jones et al. | 204/182.8 |
| 5,304,487 | A | 4/1994 | Wilding et al. | 435/291 |
| 5,480,614 | A | 1/1996 | Kamahori | 422/70 |
| 5,486,335 | A | 1/1996 | Wilding et al. | 422/55 |
| 5,498,392 | A | 3/1996 | Wilding et al. | 422/68.1 |
| 5,573,651 | A | 11/1996 | Dasgupta et al. | 204/601 |
| 5,580,435 | A | * 12/1996 | Kovacs | 204/603 |
| 5,585,069 | A | 12/1996 | Zanzucchi et al. | 422/100 |
| 5,593,838 | A | 1/1997 | Zanzucchi et al. | 435/6 |
| 5,599,432 | A | 2/1997 | Manz et al. | 204/451 |
| 5,605,662 | A | 2/1997 | Heller et al. | 422/68.1 |
| 5,800,690 | A | 9/1998 | Chow et al. | 204/451 |
| 5,846,396 | A | * 12/1998 | Zanzucchi et al. | 204/601 |
| 5,906,723 | A | * 5/1999 | Mathies et al. | 20/603 |

OTHER PUBLICATIONS

Jacobson et al., "High–Speed Separations on a Microchip," *Anal. Chem.* (1994) 66:1114–1118 Apr. 1.

Jacobson et al., "Fused Quartz Substrates for Microchip Electrophoresis," *Anal. Chem.* (1995) 67:2059–2063 Jul. 15.

Jacobson et al., "Open Channel Electrochromatography on a Microchip," *Anal. Chem.* (1994) 66:2369–2373 Jul. 15.

Jacobson et al., "Precolumn Reactions with Electrophoretic Analysis Integrated on a Microchip," *Anal. Chem.* (1994) 66:4127–4132 Dec. 2.

Jacobson et al., "Microchip electrophoresis with sample stacking," *Electrophoresis* (1995) 16:481–486 #.

Manz et al., "Electroosmotic pumping and electrophoretic separations for miniaturized chemical analysis systems," *J. Micromech. Microeng.* (1994) 4:257–265 #.

Ramsey et al., "Microfabricated chemical measurement systems," *Nature Medicine* (1995) 1:1093–1096 #.

Seiler et al., "Electroosmotic Pumping and Valveless Control of Fluid Flow within a Manifold of Capillaries on a Glass Chip," *Anal. Chem.* (1994) 66:3485–3491 Dec. 15.

Dasgupta et al., "Electroosmosis: A Reliable Fluid Propulsion System for Flow Injection Analysis," *Anal. Chem.* (1994) 66:1792–1798 #.

Linhares et al., "Use of an On–column Fracture in Capillary Zone Electrophoresis for Sample Introduction," *Anal. Chem.* (1991) 63:2076–2078 Sep. 15.

Effenhauser et al., "Glass Chips for High–Speed Capillary Electrophoresis Separations with Submicrometer Plate Heights," *Anal. Chem.* (1993) 65:2637–2642 Oct. 2.

Effenhauser et al., "High–Speed Separation of Antisense Oligonucleotides on a Micromachined Capillary Electrophoresis Device," *Anal. Chem.* (1994) 66:2949–2953 Sep. 15.

Harrison et al., "Capillary Electrophoresis and Sample Injection Systems Integrated on a Planar Glass Chip," *Anal. Chem.* (1992) 64:1926–1932 Sep. 15.

Manz et al., "Miniaturized Total Chemical Analysis Systems: a Novel Concept for Chemical Sensing," *Sensors and Actuators* (1990) B1:244–248 #.

Wooley et al., "Ultra–high–speed DNA fragment separations using microfabricated capillary array electrophoresis chips," *Proc. Natl. Acad. Sci. USA* (1994) 91:11348–11352 Nov.

* cited by examiner

VARIABLE CONTROL OF ELECTROOSMOTIC AND/OR ELECTROPHORETIC FORCES WITHIN A FLUID-CONTAINING STRUCTURE VIA ELECTRICAL FORCES

CROSS-REFERENCE TO RELATED APPLICATIONS

This application is a continuation-in-part of U.S. patent application Ser. No. 08/678,436, filed Jul. 3, 1996, now U.S. Pat. No. 5,800,690, which is incorporated herein by reference in its entirety for all purposes.

BACKGROUND OF THE INVENTION

There has been a growing interest in the manufacture and use of microfluidic systems for the acquisition of chemical and biochemical information. Techniques commonly associated with the semiconductor electronics industry, such as photolithography, wet chemical etching, etc., are being used in the fabrication of these microfluidic systems. The term, "microfluidic", refers to a system or device having channels and chambers which are generally fabricated at the micron or submicron scale, e.g., having at least one cross-sectional dimension in the range of from about 0.1 μm to about 500 μm. Early discussions of the use of planar chip technology for the fabrication of microfluidic systems are provided in Manz et al., *Trends in Anal. Chem.* (1990) 10(5):144–149 and Manz et al., *Avd. in Chromatog.* (1993) 33:1–66, which describe the fabrication of such fluidic devices and particularly microcapillary devices, in silicon and glass substrates.

Applications of microfluidic systems are myriad. For example, International Patent Appln. WO 96/04547, published Feb. 15, 1996, describes the use of microfluidic systems for capillary electrophoresis, liquid chromotography, flow injection analysis, and chemical reaction and synthesis. A related patent, U.S. Pat. No. 5,942,443 assigned to the present assignee, discloses wide ranging applications of microfluidic systems in rapidly assaying compounds for their effects on various chemical, and preferably, biochemical systems. The phrase, "biochemical system" generally refers to a chemical interaction that involves molecules of the type generally found within living organisms. Such interactions include the full range of catabolic and anabolic reactions which occur in living systems including enzymatic, binding, signaling and other reactions. Biochemical systems of particular interest include, e.g., receptor-ligand interactions, enzyme-substrate interactions, cellular signaling pathways, transport reactions involving model barrier systems (e.g., cells or membrane fractions) for bioavailability screening, and a variety of other general systems.

Many methods have been described for the transport and direction of fluids, e.g., samples, analytes, buffers and reagents, within these microfluidic systems or devices. One method moves fluids within microfabricated devices by mechanical micropumps and valves within the device. See, Published U.K. Patent Application No. 2 248 891 (Oct. 18, 1990), Published European Patent Application No. 568 902 (May 2, 1992), U.S. Pat. No. 5,271,724 (Aug. 21, 1991) and U.S. Pat. No. 5,277,556 (Jul. 3, 1991). See also, U.S. Pat. No. 5,171,132 (Dec. 21, 1990) to Miyazaki et al. Another method uses acoustic energy to move fluid samples within devices by the effects of acoustic streaming. See, Published PCT Application No. 94/05414 to Northrup and White. A straightforward method applies external pressure to move fluids within the device. See, e.g., the discussion in U.S. Pat. No. 5,304,487 to Wilding et al.

Still another method uses electric fields, and the resulting electrokinetic forces, to move fluid materials through the channels of the microfluidic system. See, e.g., Published European Patent Application No. 376 611 (Dec. 30, 1988) to Kovacs, Harrison et al., *Anal. Chem.* (1992) 64:1926–1932 and Manz et al. *J. Chromatog.* (1992) 593:253–258, U.S. Pat. No. 5,126,022 to Soane. Electrokinetic forces have the advantages of direct control, fast response and simplicity. However, there are still some disadvantages with this method of operating a microfluidic system.

Present devices use a network of channels in a substrate of electrically insulating material. The channels connect a number of fluid reservoirs in contact with high voltage electrodes. To move fluid materials through the network of channels, specific voltages are simultaneously applied to the various electrodes. The determination of the voltage values for each electrode in a system becomes complex as one attempts to control the material flow in one channel without affecting the flow in another channel. For example, in a relatively simple arrangement of four channels intersecting in a cross with reservoirs and electrodes at the ends of the channels, an independent increase of fluid flow between two reservoirs is not merely a matter of increasing the voltage differences at the two reservoirs. The voltages at the other two reservoirs must also be adjusted if their original flow and direction are to be maintained. Furthermore, as the number of channels, intersections, and reservoirs are increased, the control of fluid through the channels become more and more complex.

Also, the voltages applied to the electrodes in the device can be high, i.e., up to a level supportive of thousands of volts/cm. Regulated high voltage supplies are expensive, bulky and are often imprecise and a high voltage supply is required for each electrode. Thus the cost of a microfluidic system of any complexity may become prohibitive.

The present invention solves or substantially mitigates these problems of electrokinetic transport in a microfluidic system which uses another electrical parameter, rather than voltage, to simplify the control of material flow through the channels of the system. A high throughput microfluidic system having direct, fast and straightforward control over the movement of materials through the channels of the microfluidic system with a wide range of applications, such as in the fields of chemistry, biochemistry, biotechnology and molecular biology and numerous other fields, is possible.

SUMMARY OF THE INVENTION

The present invention provides for a microfluidic system with a plurality of interconnected capillary channels and a plurality of electrodes at different nodes of the capillary channels which create electric fields in the capillary channels to electrokinetically move materials in a fluid through the capillary channels. In accordance with the present invention, the microfluidic system is operated by applying a voltage between a first electrode and a second electrode responsive to an electrical current between the first and second electrodes to move materials therebetween. Electrical current can give a direct measure of ionic flow through the channels of the microfluidic system. Besides current, other electrical parameters, such as power, may be also used.

Furthermore, the present invention provides for time-multiplexing the power supply voltages on the electrodes of the microfluidic system for more precise and efficient control. The voltage to an electrode can be controlled by varying the duty cycle of the connection of the electrode to the power supply, varying the voltage to the electrode during the duty cycle, or a combination of both. In this manner, one power supply can service more than one electrode.

The present invention also provides for the direct monitoring of the voltages within the channels in the microfluidic system. Conducting leads on the surface of the microfluidic system have widths sufficiently narrow in a channel to prevent electrolysis. The leads are connected to voltage divider circuits also on the surface of the substrate. The divider circuit lowers the read-out voltage of the channel node so that special high-voltage voltmeters are not required. The divider circuits are also designed to draw negligible currents from the channels thereby minimizing unwanted electrochemical effects, e.g., gas generation, reduction/oxidation reactions.

The invention as hereinbefore described may be put to a plurality of different uses, which are themselves inventive, for example, as follows:

The use of a substrate having at least one channel in which a subject material is transported electrokinetically, by applying a voltage between two electrodes associated with the channel in response to a current at the electrodes.

A use of the aforementioned invention, in which the substrate has a plurality of interconnected channels and associated electrodes, subject material being transported along predetermined paths incorporating one or more of the channels by the application of voltages to predetermined electrodes in response to a current at the electrodes.

The use of a substrate having at least one channel in which a subject material is transported electrokinetically by the controlled time dependent application of an electrical parameter between electrodes associated with the channel.

A use of the aforementioned invention, wherein the electrical parameter comprises voltage, current or power.

The use of an insulating substrate having a plurality of channels and a plurality of electrodes associated with the channels, the application of voltages to the electrodes causing electric fields in the channels, and at least one conductive lead on the substrate extending to a channel location so that an electric parameter at the channel location can be determined.

A use of the aforementioned invention, wherein the conductive lead has a sufficiently small width such that a voltage of less than 1 volt, and preferably less than 0.1 volt, is created across the conductive lead at the channel location.

A use of an insulating substrate having a plurality of interconnected capillary channels, a plurality of electrodes at different nodes of the capillary channels for creating electric fields in the capillary channels to move materials electrokinetically in a fluid through the capillary channels, a power supply connected to at least one of the electrodes, the power supply having a mixing block having a first input terminal for receiving a controllable reference voltage and a second input terminal, and an output terminal; a voltage amplifier connected to the mixing block output terminal, the voltage amplifier having first and second output terminals, the first output terminal connected to the at least one electrode; and a feedback block connected to the first output terminal of the voltage amplifier, the feedback block having an output terminal connected to the second input terminal of the mixing block so that negative feedback is provided to stabilize the power supply.

The use of the aforementioned invention, in which the feedback block is also connected to the second output terminal of the voltage amplifier, the feedback block generating a first feedback voltage responsive to a voltage at the first output terminal and a second feedback voltage responsive to an amount of current being delivered to the at least one electrode through the first output terminal, the feedback block having a switch for passing the first or second feedback voltage to the mixing block responsive to a control signal so that the power supply is selectably stabilized by voltage or current feedback.

The use of a power supply for connection to at least one electrode of a microfluidic system in which the power supply has a mixing block having a first input terminal for receiving a controllable reference voltage and a second input terminal, and an output terminal; a voltage amplifier connected to the mixing block output terminal, the voltage amplifier having first and second output terminals, the first output terminal connected to the at least one electrode; and a feedback block connected to the first and second output terminals of the voltage amplifier and to the second input terminal of the mixing block, the feedback block generating a first feedback voltage responsive to a voltage at the first output terminal and a second feedback voltage responsive to an amount of current being delivered to the at least one electrode through the first output terminal, the feedback block having a switch for passing the first or second feedback voltage to the mixing block responsive to a control signal so that the power supply is selectably stabilized in voltage or current by negative feedback.

The use of a microfluidic system in which a substrate has a plurality of interconnected capillary channels, a plurality of electrodes at different nodes of the capillary channels for creating electric fields in the capillary channels to move materials electrokinetically in a fluid through the capillary channels, and a plurality of power supplies connected to each one of the electrodes, each of the power supplies capable of selectively supplying a selected voltage and a selected amount of current as a source or sink to the connected electrodes.

DETAILED DESCRIPTION OF THE INVENTION

Figure 1:
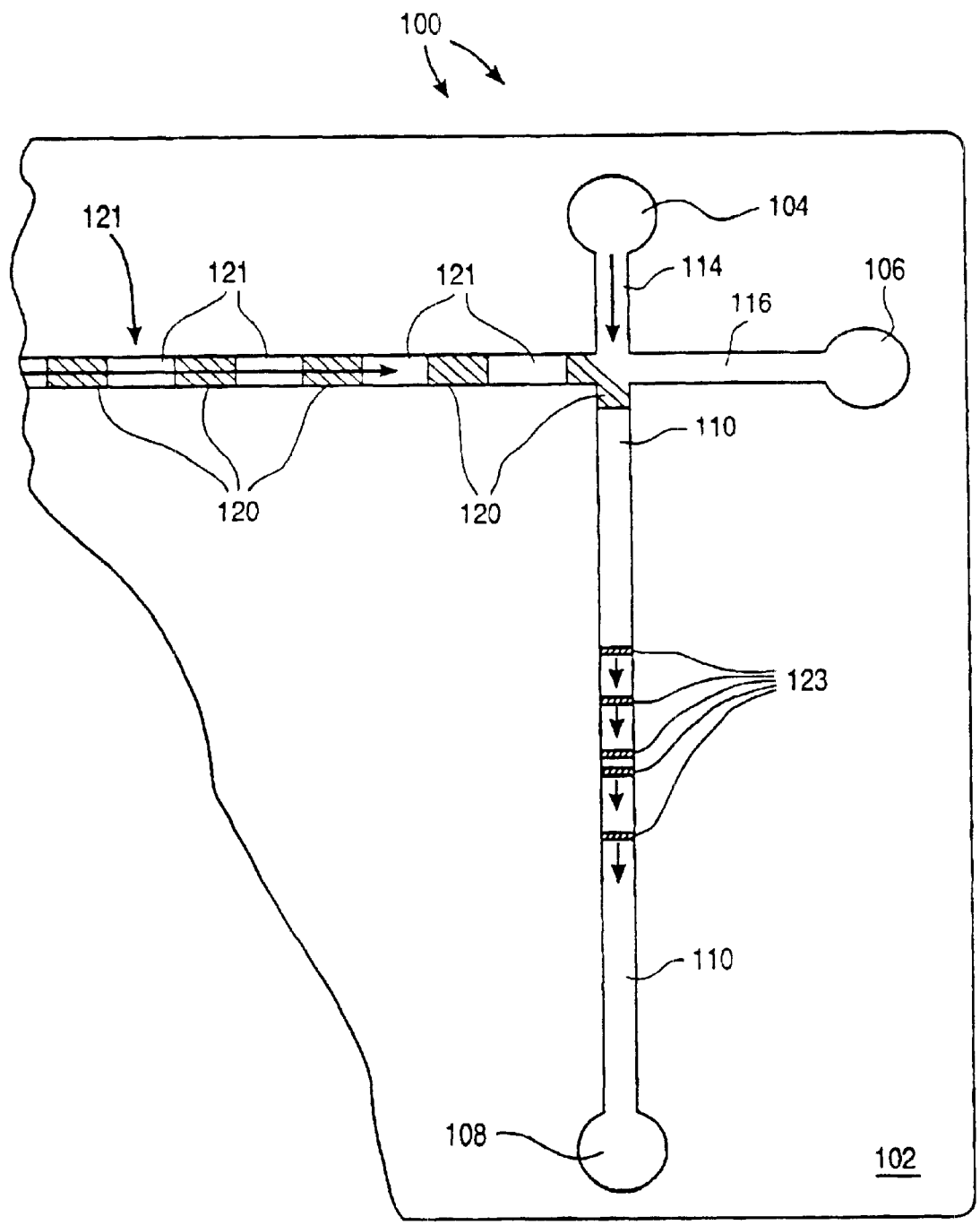
FIG. 1 shows a representative illustration of a microfluidic system.

FIG. 1 discloses a representative diagram of a portion of an exemplary microfluidic system 100 operating according to the present invention. As shown, the overall system 100 is fabricated in a planar substrate 102. Suitable substrate materials are generally selected based upon their compatibility with the conditions present in the particular operation to be performed by the device. Such conditions can include extremes of pH, temperature, ionic concentration, and application of electrical fields. Additionally, substrate materials are also selected for their inertness to critical components of an analysis or synthesis to be carried out by the system.

The system shown in FIG. 1 includes a series of channels 110, 112, 114 and 116 fabricated into the surface of the substrate 102. As discussed in the definition of "microfluidic," these channels typically have very small cross sectional dimensions. For the particular applications discussed below, channels with depths of about 10 μm and widths of about 60 μm work effectively, though deviations from these dimensions are also possible. The microfluidic system 100 transports subject materials through the various channels of the substrate 102 for various purposes, including analysis, testing, mixing with other materials, assaying and combinations of these operations. The term, "subject materials," simply refers to the material, such as a chemical or biological compound, of interest. Subject compounds may include a wide variety of different compounds, including chemical compounds, mixtures of chemical compounds, e.g., polysaccharides, small organic or inorganic molecules, biological macromolecules, e.g., peptides, proteins, nucleic acids, or extracts made from biological materials, such as bacteria, plants, fungi, or animal cells or tissues, naturally occurring or synthetic compositions.

Useful substrate materials include, e.g., glass, quartz, ceramics and silicon, as well as polymeric substrates, e.g., plastics. In the case of conductive or semiconductive substrates, there should be an insulating layer on the substrate. This is important since the system uses electroosmotic forces to move materials about the system, as discussed below. In the case of polymeric substrates, the substrate materials may be rigid, semi-rigid, or non-rigid, opaque, semi-opaque or transparent, depending upon the use for which they are intended. For example, systems which include an optical or visual detection element, are generally be fabricated, at least in part, from transparent materials to allow, or at least, facilitate that detection. Alternatively, transparent windows of glass or quartz, e.g., may be incorporated into the device for these types detection elements. Additionally, the polymeric materials may have linear or branched backbones, and may be crosslinked or non-crosslinked. Examples of particularly preferred polymeric materials include, e.g., polydimethylsiloxanes (PDMS), polyurethane, polyvinylchloride (PVC) polystyrene, polysulfone, polycarbonate, polymethylmethacrylate (PMMA) and the like.

Manufacturing of these channels and other microscale elements into the surface of the substrate 102 may be carried out by any number of microfabrication techniques that are well known in the art. For example, lithographic techniques may be employed in fabricating glass, quartz or silicon substrates, for example, with methods well known in the semiconductor manufacturing industries. Photolithographic masking, plasma or wet etching and other semiconductor processing technologies define microscale elements in and on substrate surfaces. Alternatively, micromachining methods, such as laser drilling, micromilling and the like, may be employed. Similarly, for polymeric substrates, well known manufacturing techniques may also be used. These techniques include injection molding techniques or stamp molding methods where large numbers of substrates may be produced using, e.g., rolling stamps to produce large sheets of microscale substrates or polymer microcasting techniques wherein the substrate is polymerized within a micromachined mold.

Besides the substrate 102, the microfluidic system 100 includes an additional planar element (not shown) which overlays the channeled substrate 102 to enclose and fluidly seal the various channels to form conduits. The planar cover element may be attached to the substrate by a variety of means, including, e.g., thermal bonding, adhesives or, in the case of certain substrates, e.g., glass, or semi-rigid and non-rigid polymeric substrates, a natural adhesion between the two components. The planar cover element may additionally be provided with access ports and/or reservoirs for introducing the various fluid elements needed for a particular screen.

The system 100 shown in FIG. 1 also includes reservoirs 104, 106 and 108, which are disposed and fluidly connected at the ends of the channels 114, 116 and 110 respectively. As shown, the channel 112 is used to introduce a plurality of different subject materials into the device. As such, the channel 112 is fluidly connected to a source of large numbers of separate subject materials which are individually introduced into the channel 112 and subsequently into another channel 110 for electrophoretic analysis, for example. The subject materials are transported in fluid slug regions 120 of predetermined ionic concentrations. The regions are separated by buffer regions of varying ionic concentrations and represented by buffer regions 121 in FIG. 1. Related U.S. Pat. Nos. 5,779,868 and 5,880,071 assigned to the present assignee, explain various arrangements of slugs, and buffer regions of high and low ionic concentrations in transporting subject materials with electrokinetic forces. The applications are incorporated herein by reference in their entirety for all purposes.

To move materials through the channels 110, 112, 114 and 116, a voltage controller which is capable of simultaneously applying selectable voltage levels, including ground, to each of the reservoirs, may be used. Such a voltage controller may be implemented using multiple voltage dividers and relays to obtain the selectable voltage levels. Alternatively, multiple independent voltage sources may be used. The voltage controller is electrically connected to each of the reservoirs via an electrode positioned or fabricated within each of the reservoirs 104, 106 and 108. See, for example, published International Patent Application No. WO 96/04547 to Ramsey, which is incorporated herein by reference in its entirety for all purposes.

Figure 2A:
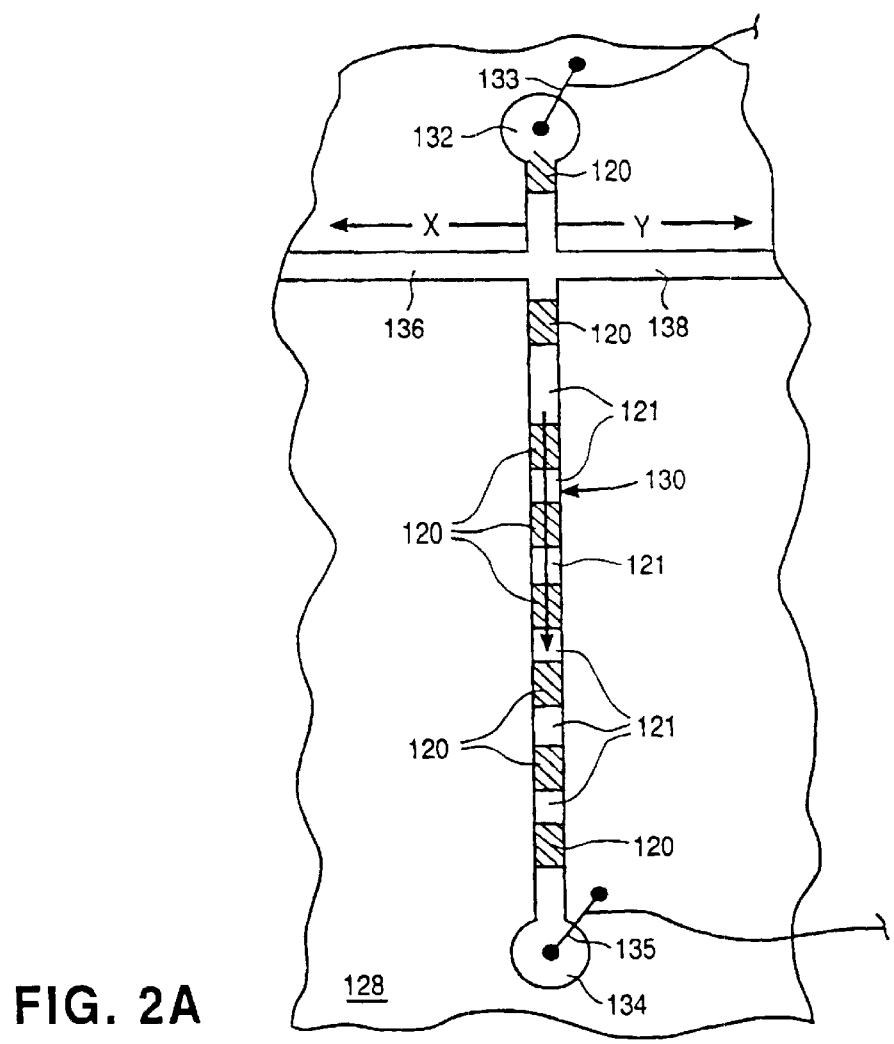
FIG. 2A illustrates an exemplary channel of a microfluidic system, such as that of FIG. 1.
Figure 2B:
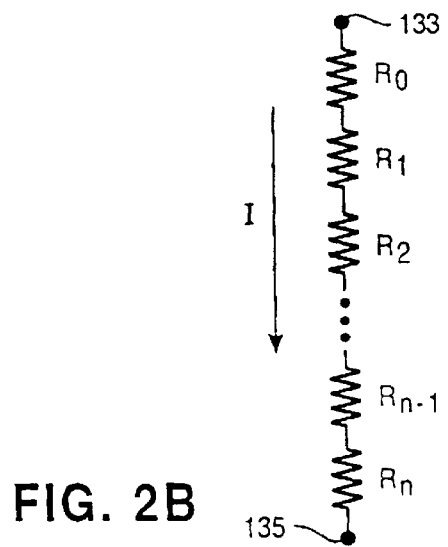
FIG. 2B represents the electrical circuit created along the channel in FIG. 2A.

Besides complexity, there are other problems with voltage control in a microfluidic system. FIG. 2A illustrates an exemplary channel 130 between two reservoirs 132 and 134, each respectively in contact with electrodes 133 and 135, connected to electrical leads are shown leading off the substrate 128. To make the example more realistic, the channel 130 is shown as being connected to two other channels 136 and 138. Operationally, the reservoir 132 is a source for slugs 120 containing the subject material. The slugs 120 are moved toward the reservoir 134, which acts as a sink. The channels 136 and 138 provide buffer regions 121 to separate the slugs 120 in the channel 130.

The different resistances of the slugs 120 and buffer regions 121 in the channel 130 create an electrical circuit which is symbolically indicated in this simple example. The voltage V applied between the two electrodes 133 and 135 is:

$$V = I \sum_{i=0}^{n} R_i$$

where I is the current between the two electrodes 133, 135 (assuming no current flow into 136, 138) and $R_i$ the resistance of the different slugs 120 and buffer regions 121.

A voltage control system is subject to many factors which can interfere with the operation of the system. For example, the contact at the interface between an electrode and fluid may be a source of problems. When the effective resistance of the electrode-to-fluid contact varies due to contaminants, bubbles, oxidation, for example, the voltage applied to the fluid varies. With V set at the electrodes, a decrease in electrode surface area contacting the solution due to bubble formation on the electrode causes an increase in resistance from the electrode to the solution. This reduces the current between electrodes, which in turn reduces the induced electroosmotic and electrophoretic forces in the channel 130.

Other problems may affect the channel current flow. Undesirable particulates may affect the channel resistance by effectively modifying the cross-sectional area of the channel. Again, with a change of channel resistance, the physical current flow is changed.

With other channels, such as channels 136 and 138, connected to the exemplary channel 130, dimensional variations in the geometry of the channels in the substrate 102 can seriously affect the operation of a voltage control system. For example, the intersection node for the channels 130, 136 and 138 might be X distance from the electrode for the reservoir at the terminus of the channel 136 (not shown) and Y distance from the electrode for the reservoir at the terminus of the channel 138 (not shown). With a slight lateral misalignment in the photolithographic process, the distances X and Y are no longer the same for the microfluidic system on another substrate. The voltage control must be recalibrated from substrate to substrate, a time-consuming and expensive process, so that the fluid movement at the intersection node can be properly controlled.

To avoid these problems, the present invention uses electric current control in the microfluidic system 100. The electrical current flow at a given electrode is directly related to the ionic flow along the channel(s) connecting the reservoir in which the electrode is placed. This is in contrast to the requirement of determining voltages at various nodes along the channel in a voltage control system. Thus the voltages at the electrodes of the microfluidic system 100 are set responsive to the electric currents flowing through the various electrodes of the system 100. Current control is less susceptible to dimensional variations in the process of creating the microfluidic system on the substrate 102. Current control permits far easier operations for pumping, valving, dispensing, mixing and concentrating subject materials and buffer fluids in a complex microfluidic system. Current control is also preferred for moderating undesired temperature effects within the channels.

Of course, besides electric current which provides a direct measure of ionic flow between electrodes, other electrical parameters related to current, such as power, may be used as a control for the microfluidic system 100. Power gives an indirect measurement of the electric current through an electrode. Hence the physical current between electrodes (and the ionic flow) can be monitored by the power through the electrodes.

Even with a current control system described above, high voltages must still be applied to the electrodes of the microfluidic system. To eliminate the need for expensive power supplies which are capable of generating continuous and precise high voltages, the present invention provides for power supplies which are time-multiplexed. These time-multiplexed power supplies also reduce the number of power supplies required for the system 100, since more than one electrode can be serviced by a time-multiplexed power supply.

Figure 3A:
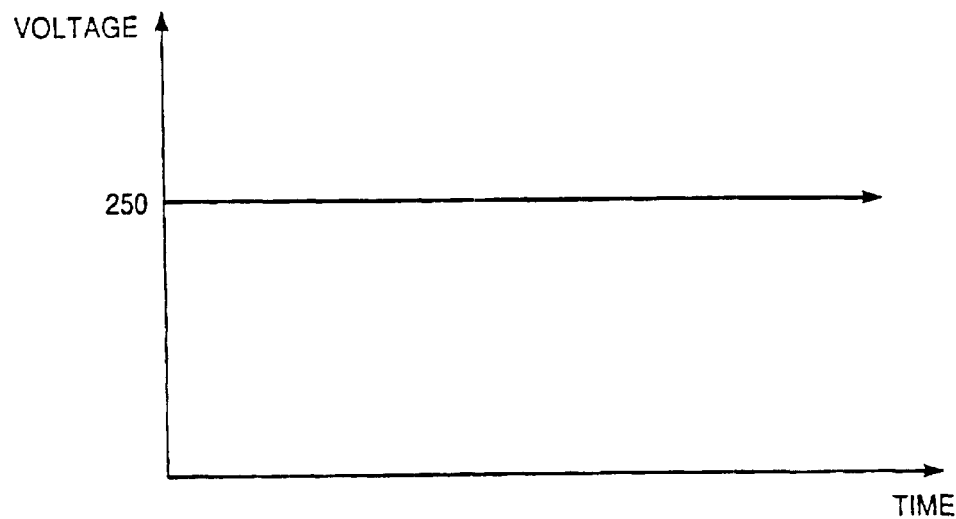
FIG. 3A is a graph of output voltage versus time for a prior art power supply.
Figure 3B:
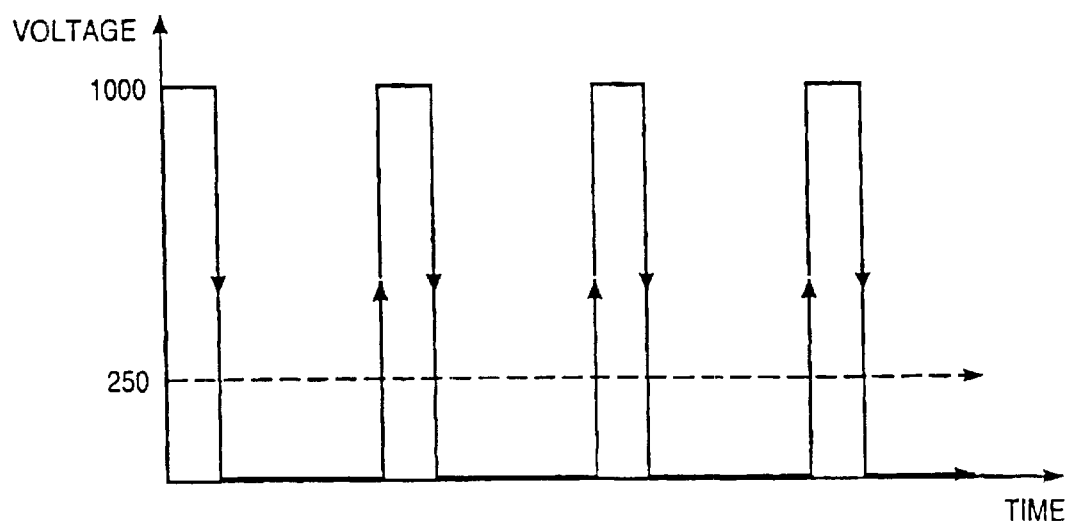
FIG. 3B is a graph of output voltage versus time for a time-multiplexed power supply according to the present invention.

FIG. 3A illustrates the exemplary output of a high power supply presently used in a electrokinetic system. The output is constant at 250 volts between two electrodes over time. In contrast, FIG. 3B illustrates the output of a power supply operating according to the present invention. To maintain a constant voltage of 250 volts, the output voltage is time-multiplexed with a one-quarter duty cycle at 1000 volts. Averaged in time, the output of the time-multiplexed voltage supply is 250 volts, as illustrated by the horizontal dotted line across the graph. Note that if the voltage must change, say, in response to current control, as discussed above, the output voltage of the time-multiplexed power supply can also change by a change in the applied voltage, or by a change in the duty cycle, or a combination of both.

Electroosmotic fluid flow can be started and stopped on the $\mu$second time scale in channels of the dimensions described here. Therefore, voltage modulation frequencies which are lower than one Megahertz result in choppy movement of the fluids. This should have no adverse effects on fluid manipulation due to the plug flow nature of electroosmotic fluid. Because most chemical mixing, incubating and separating events occur on the 0.1 to 100 second time scale, the much lower frequencies for voltage manipulation may be acceptable. As a rule of thumb, the modulation period should be less than 1% of the shortest switching event (e.g., switching flow from one channel to another) to keep mixing or pipetting errors below 1%. For a switching event of 0.1 seconds, the voltage modulation frequency should be 1 KHz or higher.

Figure 4A:
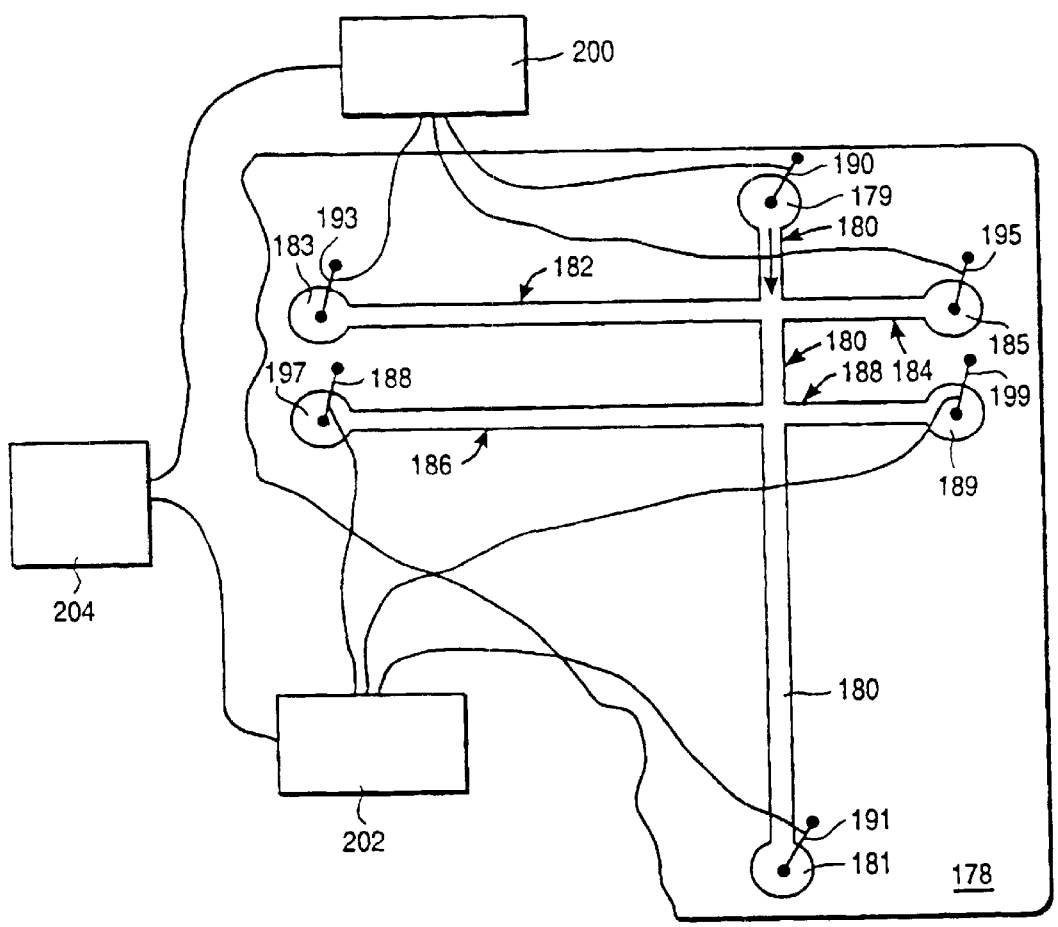
FIG. 4A is a representative illustration of a microfluidic system operating with time-multiplexed voltages according to the present invention.

FIG. 4A is a block diagram of a multiplexed power supply system with two power supplies 200 and 202 and controller block 204 for an exemplary and simple microfluidic system having a channel 180 which intersects channels 182, 184, 186 and 188. The channel 180 terminates in reservoirs 179 and 181 with electrodes 190 and 191 respectively. The channel 182 ends with a reservoir 183 having an electrode 193; the channel 184 ends with a reservoir 185 having an electrode 195; the channel 186 with reservoir 187 having an electrode 197; and the channel 188 with reservoir 189 having an electrode 199.

The power supplies 200 and 202 are connected to the different electrodes 190, 191, 193, 195, 197 and 199 of the microfluidic system. The power supply 200 is connected to three electrodes 190, 193 and 195, and the power supply 202 is connected to the remaining three electrodes 191, 197 and 199. The controller block 204 is connected to each of the power supplies 200 and 202 to coordinate their operations. For instance, to control the movements of fluids through the channels 182, 184, 186 and 188, the voltages on the electrodes 190, 191, 193, 195, 197 and 199 must be properly timed. The voltages on the electrodes change in response to electric current flow, as described above, for example, as the controller block 204 directs the power supplies 200 and 202.

Figure 4B:
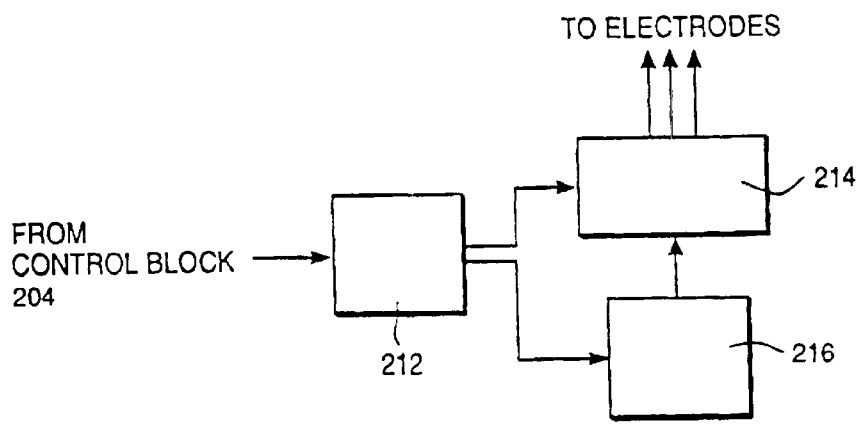
FIG. 4B is a block diagram illustrating the units of a power supply in FIG. 4A.

Each of the power supplies 200 and 202 are organized into units illustrated in FIG. 4B. A control unit 212 receives control signals from the control block 204 and directs the operation of a switching unit 214. The switching unit 214, connected to a power supply unit 216, makes or breaks connections of the power supply unit 216 to the connected electrodes. In other words, the switching unit 214 time-multiplexes the power from the power supply unit 216 among its connected electrodes. The power supply unit 216 is also connected to the control unit 212 which directs the variation of output from the power supply unit 216 to the switching unit 214. In an alternate arrangement, this connection to the control unit 212 is not required if the power supply unit 216 supplies a constant voltage and the averaged voltage to a electrode is changed by varying connection duty cycle through the switching unit 214.

Figure 6A:
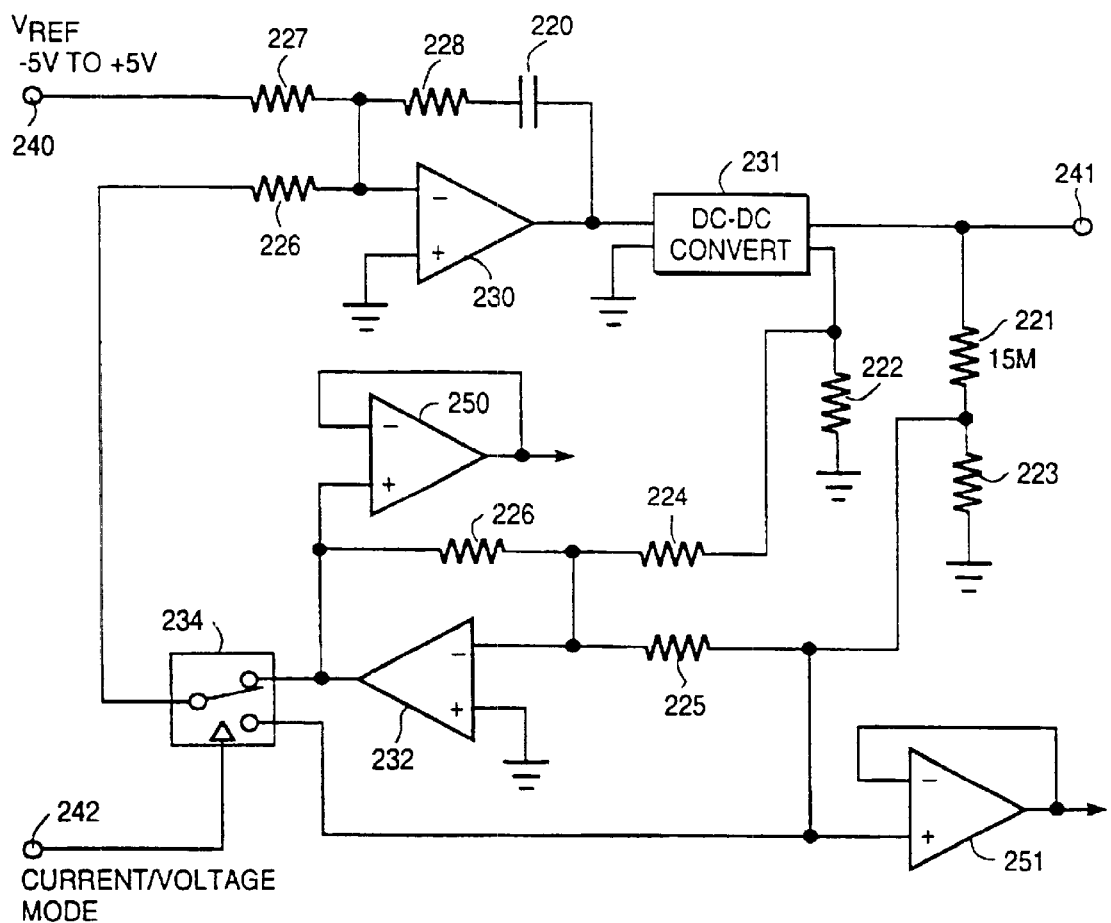
FIG. 6A is a block diagram of the power supply unit of FIG. 4B.

FIG. 6A is a block diagram of a power supply which could be used as the power supply unit 216 in FIG. 4B. Alternatively, the illustrated power supply may be connected directly to an electrode of a microfluidic system if time-multiplexing is not used. The power supply can supply a stable voltage to an electrode or to supply, or sink, a stable current.

The power supply has an input terminal 240 which is supplied with a controllable reference voltage from −5 to +5 volts, which is stepped up in magnitude to hundreds of volts at an output terminal 241. The input terminal is connected to the negative input terminal of an input operational amplifier 230 through an resistance 227. The positive input terminal of an operational amplifier 230 is grounded and its output terminal is connected back to the negative input terminal through a feedback capacitor 220 and resistor 228 connected in series. The output terminal is also connected to an input terminal of a DC-to-DC converter 231. A second input terminal is grounded. The output side of the converter 231, which steps up the voltage received from the amplifier 230, is connected to the power supply output terminal 241. The second output terminal of the converter 231 is grounded through a resistor 222.

The power supply output terminal 241 is also connected to ground through two series-connected resistances 221 and 223 which form a voltage divider circuit. The node between the two resistances 221 and 223 is connected to one input terminal of a current/voltage mode switch 234. The node is also connected to the negative input terminal of a feedback operational amplifier 232 through a resistance 225. The negative input terminal is also connected to the output terminal of the converter 231 through a resistor 224 and to the output terminal of the amplifier 232 through a feedback resistor 226. The output terminal of the amplifier 232 is also connected to a second input terminal of the switch 234, which has its output terminal connected to the negative input terminal of the input operational amplifier 230 through a resistor 226.

The switch 234 is responsive to a signal on the control terminal 242. As shown in FIG. 6A, the switch 234 connects its output terminal to either the output terminal of the feedback operational amplifier 232, or the voltage divider node between the two resistors 221 and 223. The connection determines whether the power supply circuit operates in the voltage mode (connection to the voltage divider node) or in the current mode (connection to the output of the feedback operational amplifier 232). Note that the resistor 221 is very large, approximately 15 MΩ, so that the voltage on the output terminal 241 can be easily fed back when the power supply is operated.

The FIG. 6A circuit may be separated into different operational blocks. The operational amplifier 230, resistors 226–228 and capacitor 220 are part of a mixing block. The mixing block accepts the controllable reference voltage $V_{ref}$, about which the power supply operates, at the input terminal 240 and a feedback voltage, discussed below, to generate an output voltage, a combination of $V_{ref}$ and feedback voltages, for the DC—DC converter 231. The converter 231, illustrated as a voltage amplifier in FIG. 6B, simply amplifies the voltage from the operational amplifier 230. One output terminal of the voltage amplifier is connected to the output terminal 241 and a terminal of the resistor 221. The other output of the voltage amplifier is connected to ground through the resistor 222. The resistors 221–223 may be considered as part of a feedback block which also has resistors 224–226 and operational amplifier 232. The switch 234 is also part of the feedback block and is connected to the second input terminal of the mixing block, as described previously.

Operationally, the mixing block has the operational amplifier 230 which is connected as a summing amplifier with the resistances 226–228. With the capacitor 220 in the feedback loop of the operational amplifier 230, the output voltage of the operational amplifier 230 is the voltage integrated over time of the sum (or difference) of the reference voltage $V_{ref}$ and the feedback voltage from the switch 234. Of course, the reference voltage $V_{ref}$ and feedback voltage may be selectively weighted by the values of the resistances 226 and 227. The capacitor 220 and the amplifier 230 also act as a filter to remove high frequency fluctuations from the power supply.

Figure 6B:
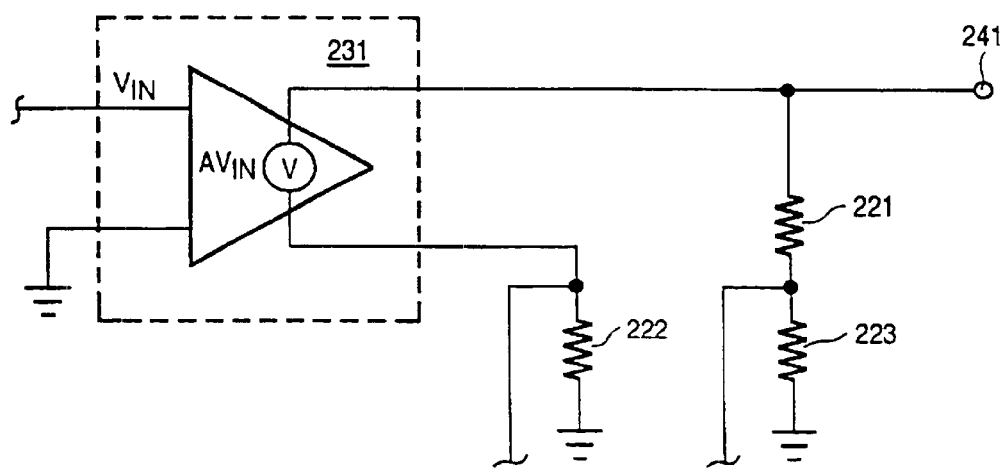
FIG. 6B is an amplifier block representation of the DC—DC converter block of FIG. 6A.

The output signal from the operational amplifier 230 may be conditioned, for example, rectified or buffered, by additional elements (not shown). Nonetheless, for purposes of understanding this invention, $V_{IN}$, the voltage received by the DC—DC converter 231, can be considered the same as the output voltage of the operational amplifier 230. As shown in FIG. 6B, $V_{IN}$ is amplified by a gain factor A and the amplified voltage $AV_{IN}$ is generated on the output terminal 241.

The feedback block has a voltage divider circuit formed by the resistors 221 and 223 connected between the output terminal 241 and ground. The voltage at the node between the resistors 221 and 223 is directly proportional to the voltage at the output terminal 241. When the switch 234 in response to the signal on the control terminal 242 selects the voltage feedback mode, the node voltage is fed directly back to the mixing block and the operational amplifier 230. The negative feedback stabilizes the output at the terminal 241. For example, if the voltage at the terminal 241 is high, the feedback voltage is high. This, in turn, causes the output voltage of the operational amplifier 230 to drop, thus correcting for the high voltage at the output terminal 241. For monitoring the voltage at the output terminal 241, the node is also connected to an operational amplifier 251, configured as a simple buffer, to send the feedback voltage to a monitoring circuit (not shown).

The feedback block also has the operational amplifier 232 and the resistances 224–226 which are connected to configure the operational amplifier 232 as a summing amplifier. One input to the summing amplifier is connected to the node between the resistors 221 and 223. The second input is connected to the node between the resistor 222 connected to ground and the second output terminal of the DC—DC converter 231. The summing amplifier measures the difference between the amount of current through the series-connected resistors 221 and 223 and through the converter 231 (the total current through the resistors 222 and 224). In effect, the summing amplifier measures the amount of current being delivered through the output terminal 241. Thus when the switch 234 is set in the current feedback mode, the output from the operational amplifier 232 acting as a summing amplifier is sent to the mixing block and the power supply circuit is stabilized about the amount of current being delivered through the power supply terminal 241 to a connected electrode of a microfluidic system.

The output of the summing amplifier is also connected to an operational amplifier 250, configured as a simple buffer, to send the output voltage to the monitoring circuit (not shown). From the outputs of the operational amplifiers 250 and 251, the monitoring circuit has a measure of the voltage at the output terminal 241 and of the current through the terminal. This also allows the monitoring circuit to determine, and to regulate, the amount of power being supplied by the power supply circuit.

The ability of the described power supply to act as a variable source allows the direction of fluid flow through the microchannels of a microfluidic system to be changed electronically. If all of the electrodes are connected to one or more of the power supplies described above, operation of the microfluidic system is greatly enhanced and the desired movements of fluids through the network of channels in the system are much more flexible.

Figure 5A:
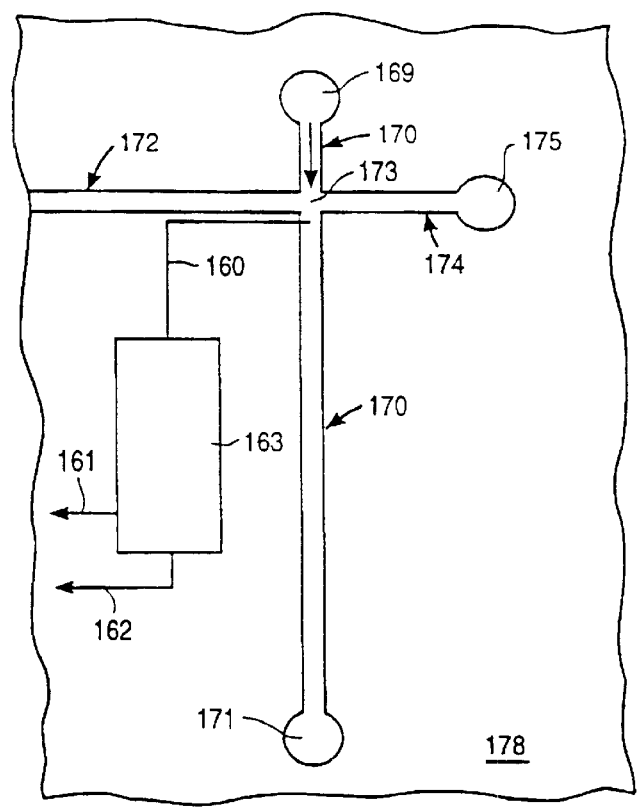
FIG. 5A is a representative illustration of a microfluidic system with voltage-monitored nodes according to the present invention.

Despite operation as a current control system, there is often still a need to determine the voltage at a node in a microfluidic system. The present invention also provides a means for such voltage monitoring. As shown in FIG. 5A, an electrical lead 160 is formed on the surface of a substrate 178 near a desired node 173 in the microfluidic system. The node 173 is at the intersection of channel 170 having reservoirs 169 and 171 at each end and channels 172 and 174. The terminus of the channel 174 has a reservoir 175, while the terminus of the channel 172 (and a reservoir) is not shown.

The lead 160 is preferably formed by the deposition of a conductive metal, or metal alloy, preferably a noble metal, such as gold on chrome or platinum on titanium, used in integrated circuits. With semiconductor photolithography techniques, the lead 160 may be defined with widths of less than 1 $\mu$m. To prevent electrolysis, the width of the lead 160 in the channel 170 is narrow enough such that the voltage across the lead in the channel 170 should be less than 1 volt, preferably less 0.1 volt, at all times.

The voltages used in the microfluidic system are high. A voltmeter directly measuring the voltage at the channel node 173 through the lead 160 must have a very high input impedance to be capable of measuring such high voltages. Such voltmeters are expensive. Furthermore, handling of the substrate of the microfluidic systems increases the possibility of contamination. Such contamination can seriously affect the voltages (and electric fields) required for proper operation of electrokinetic forces in the channels of the microfluidic system.

To avoid these problems and costs, the lead 160 is connected to a voltage divider circuit 163, which is also formed on the surface of the substrate 178. The output of the voltage divider circuit 163 is carried by a conductive output lead 161. The circuit 163 is also connected by a conductive lead 162 to a voltage reference.

Figure 5B:
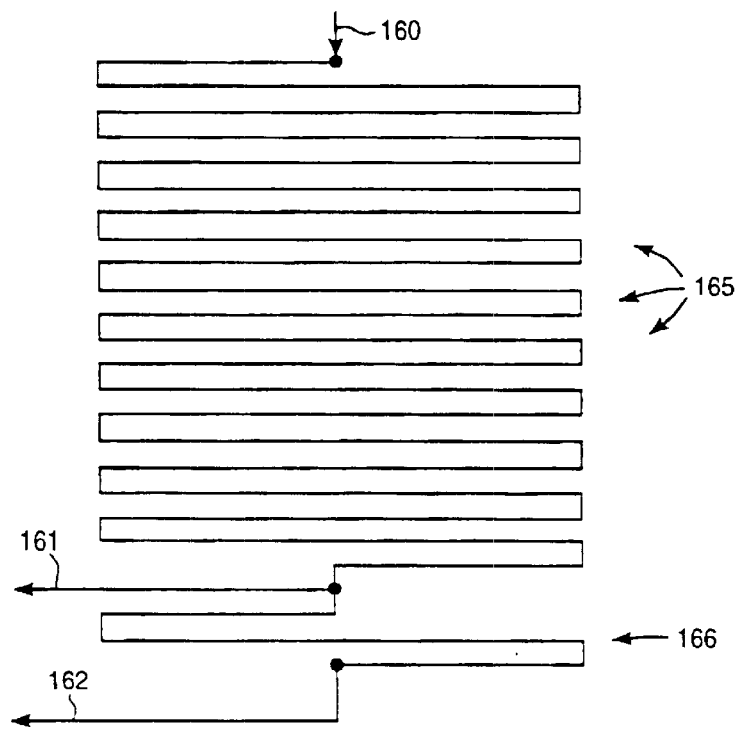
FIG. 5B details the voltage divider circuit of FIG. 5A.

The voltage divider circuit 163, shown in greater detail in FIG. 5B, is formed with standard semiconductor manufacturing technology with resistors 165 and 166 connected as a voltage divider circuit. The lead 160 is connected to the input terminal of the circuit 163, which is one end of a linear pattern of high-resistance material, such as undoped or lightly doped polysilicon or alumina. The other end of the linear pattern is connected to the reference lead 162, which is also formed on the substrate 168 and leads to an external reference voltage, presumably ground. As shown for explanatory purposes, the voltage of the lead 160 is divided in a 10-to-1 ratio. The linear pattern is divided into a resistor 165 and a resistor 166. The resistor 165 has nine times more loops than the resistor 166, i.e., the resistance of the resistor 165 is nine times greater than the resistance of the resistor 166. Of course, other ratios may be used and a 1000:1 ratio is typical. The output lead 161, connected between the two resistors 165 and 166, leads to an external connection for a low-voltage reading by a voltmeter. The cover plate then protects the leads 160–162, the voltage divider circuit 163 and the surface of the substrate from contamination.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. A microfluidic system comprising
a plurality of capillary channels in an insulated substrate;
a plurality of electrodes at different nodes of said capillary channels for creating electric fields in said capillary channels to electrokinetically flow materials in a fluid through said capillary channels;
at least one variable voltage controller operably coupled to said plurality of electrodes which is configured to control an applied voltage at said plurality of electrodes in response to a measure of electric current flow at said plurality of electrodes; and
at least one conductive lead on said substrate extending to a capillary channel location for determining a voltage level at said location due to said applied voltage.

2. The microfluidic system of claim 1 wherein said conductive lead is dimensioned such that a voltage across the lead in the capillary channel is less than about 1 volt due to said applied voltage.

3. The microfluidic system of claim 1 wherein said conductive lead is dimensioned such that a voltage across the lead in the capillary channel is less than about 0.1 volt due to said applied voltage.

4. The microfluidic system of claim 1 wherein said conductive lead is arranged to form a voltage divider circuit on said substrate so that voltage received from said conductive lead is a fraction of said voltage at said capillary channel location.

5. The microfluidic system of claim 1 further comprising an insulating plate covering said substrate, said conductive lead extending to an edge of said substrate.

6. The microfluidic system of claim 1 wherein said variable voltage controller comprises at least one time-multiplexed power supply.

7. The microfluidic system of claim 6 further comprising two or more time-multiplexed power supplies.

8. The microfluidic system of claim 7 wherein each of said two or more power supplies are operably coupled to three or more electrodes.

9. The microfluidic system of claim 1 wherein said conductive lead has a width of less than about 1 $\mu$m.

10. The microfluidic system of claim 1 wherein said conductive lead has a width sufficiently narrow along said capillary channel to avoid electrolysis due to said applied voltage.

11. A method of a manufacturing a microfluidic system comprising disposing a plurality of capillary channels in an insulating substrate;

selecting a plurality of different nodes of said capillary channel to receive electrodes, said electrodes being capable of creating electric fields in said capillary channels in response to an applied voltage to said electrodes to electrokinetically flow materials in a fluid through said capillary channels;

fixing a plurality of electrodes at said different nodes of said capillary channels;

connecting said electrodes to at least one variable voltage controller which is configured to control the applied voltage at said electrodes in response to a measure of electric current flow at said electrodes; and disposing at least one conductive lead on said substrate to a capillary channel location to determine a voltage at said capillary channel location due to said applied voltage at said plurality of electrodes.

12. The method of claim 11 wherein in said conductive lead disposing step, said conductive lead is dimensioned such that a voltage across the lead in the capillary channel is less than about 1 volt due to said applied voltage.

13. The methods of claim 12 wherein in said conductive lead disposing step, said conductive lead is dimensioned such that a voltage across the lead in the capillary channel is less than about 0.1 volt due to said applied voltage.

14. The method of claim 11 wherein said conductive lead disposing step further comprises arranging said conductive lead to form a voltage divider circuit on said substrate so that voltage received from said conductive lead is a fraction of said voltage at said capillary channel location.

15. The method of claim 11 wherein said conductive lead disposing step further comprises extending said conductive lead to an edge of said substrate, and further comprising covering said substrate with an insulating plate.

* * * * *